(12) United States Patent
Ouchi

(10) Patent No.: US 6,852,078 B2
(45) Date of Patent: Feb. 8, 2005

(54) OUTER SHEATHED ENDOSCOPE

(75) Inventor: Teruo Ouchi, Saitama (JP)

(73) Assignee: PENTAX Corporation, Tokyo (JP)

( * ) Notice: Subject to any disclaimer, the term of this patent is extended or adjusted under 35 U.S.C. 154(b) by 21 days.

(21) Appl. No.: 10/439,009

(22) Filed: May 16, 2003

(65) Prior Publication Data

US 2003/0220545 A1 Nov. 27, 2003

(30) Foreign Application Priority Data

| May 22, 2002 | (JP) | ................................ P 2002-147158 |
| May 24, 2002 | (JP) | ................................ P 2002-149992 |
| May 27, 2002 | (JP) | ................................ P 2002-151982 |

(51) Int. Cl.$^7$ ................................................ A61B 1/00
(52) U.S. Cl. ........................ 600/139; 600/121; 600/140; 600/128
(58) Field of Search ................................ 600/121, 122, 600/123, 124, 125, 131, 139, 140, 138, 128

(56) References Cited

U.S. PATENT DOCUMENTS

| 4,991,565 A |   | 2/1991 | Takahashi et al. |            |
| 5,536,235 A | * | 7/1996 | Yabe et al. ................. | 600/121 |
| 5,863,287 A | * | 1/1999 | Segawa ....................... | 600/121 |
| 6,174,280 B1 | * | 1/2001 | Oneda et al. ................. | 600/121 |
| 6,458,075 B1 | * | 10/2002 | Sugiyama et al. ........... | 600/139 |
| 2003/0149339 A1 | * | 8/2003 | Ishibiki ...................... | 600/160 |

FOREIGN PATENT DOCUMENTS

| JP | 6-63005 | 9/1994 |
| JP | 6-68708 | 9/1994 |
| JP | 6-98115 | 12/1994 |
| JP | 2641789 | 5/1997 |
| JP | 2750613 | 2/1998 |
| JP | 2604558 | 3/2000 |
| JP | 2605549 | 5/2000 |

OTHER PUBLICATIONS

English Language Translation of JP Appln. No. 6–98115.
English Language Translation of JP Appln. No. 2–641789.
English Language Translation of JP Appln. No. 6–63005.
English Language Translation of JP Appln. No. 6–68708.

* cited by examiner

Primary Examiner—Beverly M. Flanagan
(74) Attorney, Agent, or Firm—Greenblum & Bernstein, P.L.C.

(57) ABSTRACT

In an outer sheathed endoscope, an outer sheath (20) for shielding a flexible insertion portion (11, 12, 13) from the outside is disposed to detachably cover the flexible insertion portion (11, 12, 13). The basal end of the flexible insertion portion is connected to an operation portion (15). In the outer sheathed endoscope, A break prevention member (100) which is formed by an elastic material is disposed to surround a basal end part of the flexible insertion portion (11, 12, 13), and the outer sheath (20) is formed to cover continuously the flexible insertion portion (11, 12, 13) and the break prevention member (100).

11 Claims, 13 Drawing Sheets

OUTER SHEATHED ENDOSCOPE

BACKGROUND OF THE INVENTION

The present invention relates to an outer sheathed endoscope in which an outer sheath for preventing an insertion portion from directly contacting with the body wall of a patient is detachably disposed.

In an outer sheathed endoscope, generally, an outer sheath for shielding a flexible insertion portion of the endoscope from the outside is formed so as to detachably cover the flexible insertion portion. When the outer sheath is replaced with a new one for each use, it is possible to completely eliminate infection among patients through the endoscope.

Such an outer sheathed endoscope is configured so that a flexible insertion portion whose outer diameter is substantially constant is simply coupled to an operation portion, thereby enabling the flexible insertion portion to be completely covered with an outer sheath to the extent of reaching a coupling end with the operation portion.

In the configuration in which a flexible insertion portion is simply coupled to an operation portion as described above, however, when the flexible insertion portion is sharply bent in the vicinity of a coupling portion with the operation portion, the flexible insertion portion sometimes buckles or breaks in a relatively easy manner in both a used state where an outer sheath is attached, and a stored state where an outer sheath is not attached.

SUMMARY OF THE INVENTION

It is an object of the invention to provide an outer sheathed endoscope which has excellent durability, and in which a flexible insertion portion does not easily buckle or break in the vicinity of a coupling portion with an operation portion in both a used state where an outer sheath is attached, and a stored state where an outer sheath is not attached.

In order to solve the aforesaid object, the invention is characterized by having the following arrangement.

Aspect 1

An outer sheathed endoscope comprising:

an operation portion;

a flexible insertion portion, a basal end of which is connected to the operation portion;

a first break prevention member formed of an elastic material, which is disposed to surround a basal end portion of the flexible insertion portion and attached to the operation portion; and an outer sheath for shielding the flexible insertion portion form an outside detachably covering the flexible insertion portion and at least a part of the first break prevention member.

Aspect 2

The outer sheathed endoscope according to the aspect 1, wherein the outer sheath continuously covers the flexible insertion portion and the first break prevention member.

Aspect 3

The outer sheathed endoscope according to the aspect 1, wherein the first break prevention member is formed into a tapered shape in which an outer diameter is gradually reduced, and the outer sheath is formed into a shape in which the outer sheath in the vicinity of the basal end is gradually spread as advancing toward an end part.

Aspect 4

The outer sheathed endoscope according to the aspect 4, wherein the outer sheath covers whole of the first break prevention member.

Aspect 5

The outer sheathed endoscope according to the aspect 1, wherein the first break prevention member a sheath mounting seat which is detachably engaged with an end of the outer sheath.

Aspect 6

The outer sheathed endoscope according to the aspect 5, wherein the sheath mounting seat is one of a groove and a step formed on an outer peripheral face of a tip end part of the first break prevention member.

Aspect 7

The outer sheathed endoscope according to the aspect 5, wherein the sheath mounting seat and the first break prevention member are integrally formed of same material.

Aspect 8

The outer sheathed endoscope according to the aspect 1, wherein the outer sheath includes a second break prevention member.

Aspect 9

The outer sheathed endoscope according to the aspect 8, wherein the second break prevention member surrounds the first break prevention member when the outer sheath is attached to the flexible insertion portion.

Aspect 10

The outer sheathed endoscope according to the aspect 8, wherein one of the first and second break prevention member has a constant thickness, and the other of the first and second break prevention member has a thickness which is gradually decreases toward an end thereof.

Aspect 11

The outer sheathed endoscope according to the aspect 1, wherein the outer sheathed and the first break prevention member are made of different material.

BRIEF DESCRIPTION OF THE DRAWINGS

FIG. 1 is a side view partly in section showing the whole configuration of a stored state of an outer sheathed endoscope of a first embodiment of the invention.

DETAILED DESCRIPTION OF PREFERRED EMBODIMENTS

Embodiments according to the invention will be described with reference to the accompanying drawings.

First Embodiment

Referring to FIG. 1, 10 denotes an endoscope, and 20 denotes an outer sheath which detachably covers flexible insertion portions 11, 12 and 13 of the endoscope 10 in order to insulate the flexible insertion portions 11, 12 and 13 from the external environment in a used state.

The flexible insertion portions 11, 12, and 13 of the endoscope 10 are configured in the following manner. The bend portion 12 which can be bent by a remote operation is coupled to the tip end of the long flexible tube portion 11. The tip end body portion 13 in which an observation window 14 and the like are placed in the tip end face is coupled to the tip end of the bend portion 12.

Parts such as a bending operation knob 16 which remotely bends the bend portion 12 are placed in an operation portion 15 which is coupled to the basal end of the flexible tube portion 11. When the bending operation knob 16 is rotated, the bend portion 12 is bent.

A break prevention member 100 which is formed by an elastic material into a tapered tubular shape in which the outer diameter is gradually reduced is attached so as to surround a basal end part of the flexible tube portion 11. The reference numeral 101 denotes an attachment socket which is made of a metal, and which is formed integrally with the break prevention member 100.

As shown in detail in FIG. 3 which will be described later, the break prevention member 100 is formed into a shape in which the thickness is gradually reduced as advancing toward the tip end. As indicated by the two-dot chain line in FIG. 1, even when the flexible tube portion 11 is bent in a stored state of the endoscope 10, the break prevention member 100 functions so as not to cause the coupling portion with the operation portion 15 to be sharply bent, thereby preventing the flexible tube portion 11 from buckling or breaking.

A guide conduit 17 which is formed by, for example, a flexible polyethylene resin tube is placed so as to elongate from the interiors of the flexible insertion portions 11, 12, and 13 to the interior of the operation portion 15. A tip end opening 17a of the guide conduit 17 is formed in the tip end face of the tip end body portion 13.

A forceps port member 30 is placed at a position which is opposed to a basal end opening of the guide conduit 17 and is placed in the operation portion 15. A forceps plug 32 is attached to an insertion port of the forceps port member 30.

In the outer sheath 20, a cover tube 21 which is formed into a thin cylindrical shape by an elastic material, such as a silicone rubber tube, is disposed so as to detachably cover the flexible tube portion 11 and the bend portion 12 of the endoscope 10. An end cap 22 which is formed by a transparent member, and which is to cover the tip end body portion 13 is watertightly attached to the tip end of the tube.

A coupling ring 24 fixed to the basal end of the cover tube 21 is detachably engageable with a coupling portion 19 between the operation portion 15 of the endoscope 10 and the flexible tube portion 11. A fixing mechanism 25 can be arbitrarily engaged with a circumferential groove 19a which is formed in the coupling portion 19.

As shown in detail also in FIG. 3 which will be described later, a basal end neighboring portion 21a of the cover tube 21 which is coupled to the coupling ring 24 is formed into a shape in which the diameter is gradually spread as advancing toward the end in conformity with the shape of the break prevention member 100.

A flexible channel tube 23 (in the embodiment, a treatment tool insertion channel) which is formed by, for example, a flexible tetrafluoroethylene resin tube is passed through the whole length of the cover tube 21.

The tip end of the flexible channel tube 23 is fixed to the end cap 22 so as to be opened to the outer face in the end face of the end cap 22. A basal end part 23a of the flexible channel tube 23 elongates rearward with passing through the coupling ring 24.

The flexible channel tube 23 is insertable and extractable over the whole length of the guide conduit 17 of the endoscope 10. As indicated by the arrow of the long-short dash line, the basal end part 23a of the flexible channel tube 23 can be inserted into the tip end opening 17a of the guide conduit 17 and can be pulled out from the basal end opening.

Figure 2:
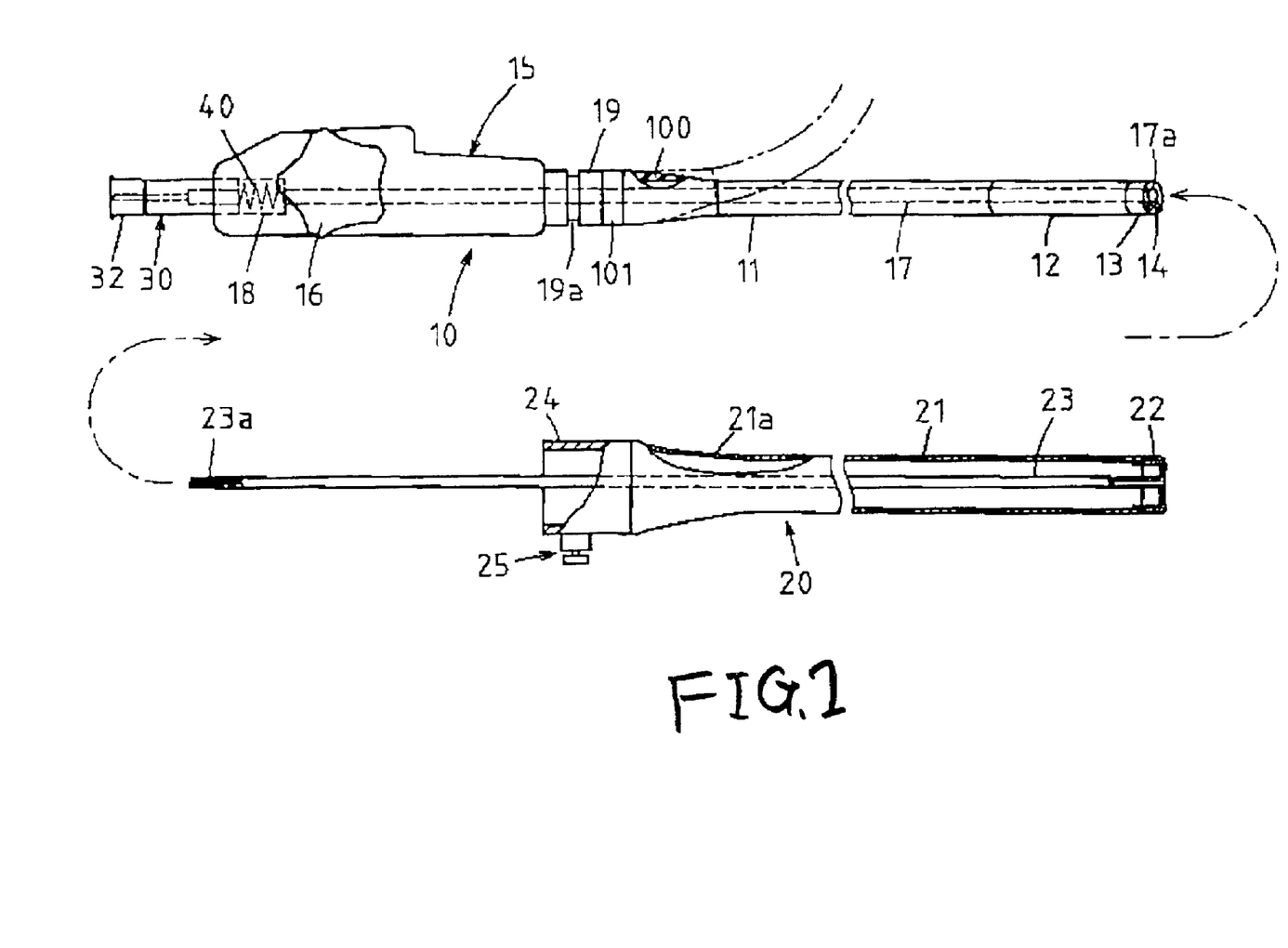
FIG. 2 is a side view partly in section showing the whole configuration of a used state of the outer sheathed endoscope of the first embodiment of the invention.

FIG. 2 shows the used state where the outer sheath 20 covers the flexible insertion portions 11, 12, and 13 of the endoscope 10 so that the end cap 22 abuts against the tip end face of the tip end body portion 13.

In this state, as described above, the coupling ring 24 of the outer sheath 20 is fixed to the coupling portion 19 of the endoscope 10, and the basal end neighboring portion 21a of the cover tube 21 covers the break prevention member 100, thereby forming a state where the flexible insertion portions 11, 12, and 13 and the break prevention member 100 are continuously covered with the outer sheath 20.

Figure 3:
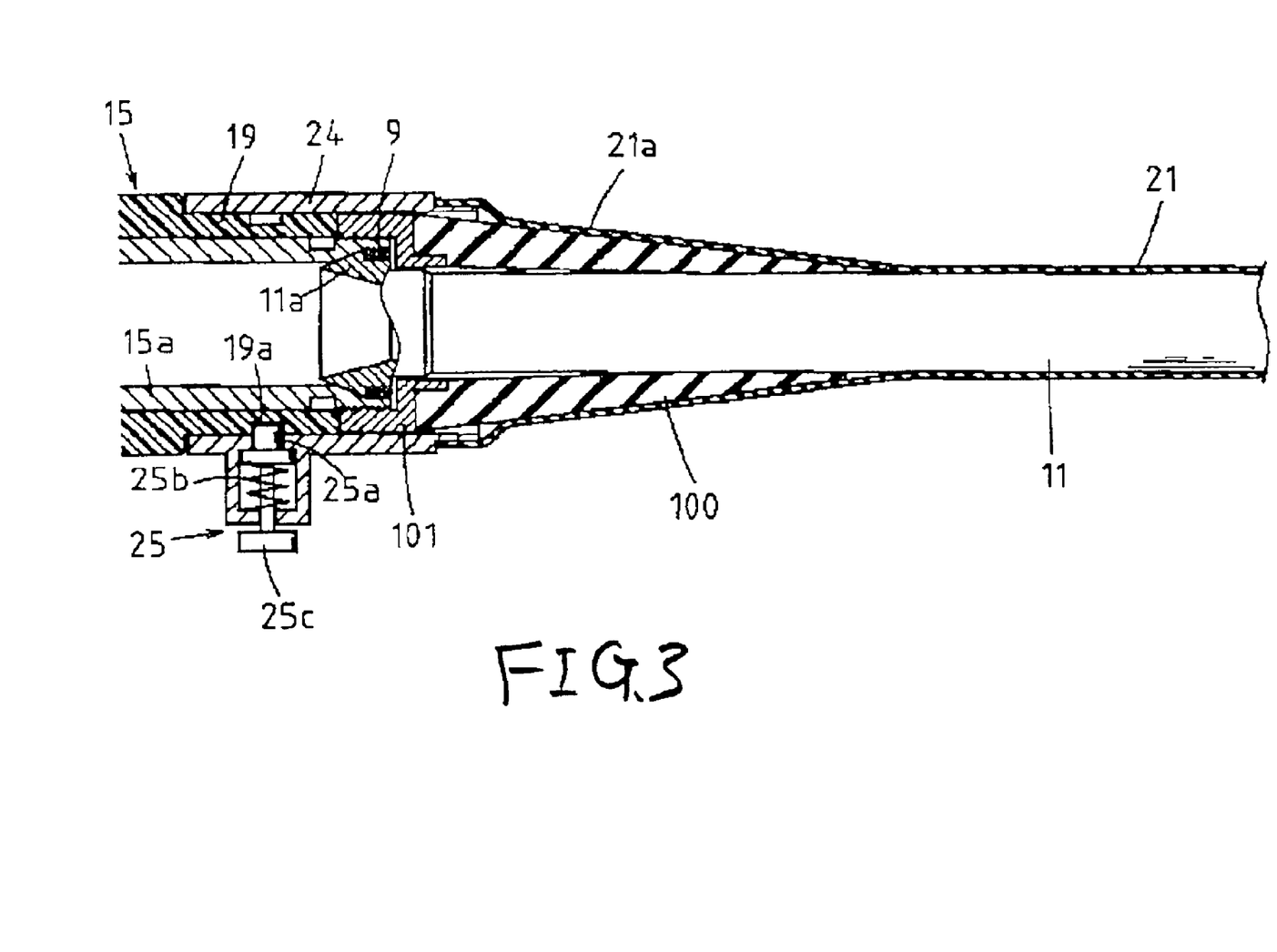
FIG. 3 is a side section view of the vicinity of a break prevention member in the used state of the outer sheathed endoscope of the first embodiment of the invention.

FIG. 3 shows in detail the vicinity of the break prevention member 100 in the used state. The incorporated articles such as the flexible channel tube 23 are not shown in the figure. In the flexible tube portion 11, a basal end socket 11a is fixed to a frame 15a of the operation part 15 by a pressing ring 9 which is screwed to an end portion of the frame 15a.

The attachment socket 101 which is integrated with the break prevention member 100 is screwed to and fixed to the frame 15a of the operation portion 15. When the screw fixation is loosed, the break prevention member 100 can be detached from the flexible tube portion 11.

The fixing mechanism 25 has a configuration in which an engagement pin 25a to be engaged with the circumferential groove 19a of the coupling portion 19 is inwardly urged by a compression coil spring 25b. When a knob 25c which outwardly protrudes is pulled up by fingers, the engagement pin 25a can be disengaged from the circumferential groove 19a.

Since the basal end neighboring portion 21a of the cover tube 21 is formed into the shape in which the diameter is gradually spread as advancing toward the end in conformity with the shape of the break prevention member 100, the flexible tube portion 11 and the break prevention member 100 are covered smoothly and continuously by the cover tube 21. According to the configuration, in the used state of the endoscope, not only the surface of the flexible tube portion 11 but also the break prevention member 100 is insulated from a contaminated area.

As indicated by the tow-dot chain line in FIG. 2, even when the flexible tube portion 11 of the endoscope 10 is bent in the used state, the break prevention member 100 functions so as not to cause the coupling portion with the operation portion 15 to be sharply bent, thereby preventing the flexible tube portion 11 from buckling or breaking.

Figure 4:
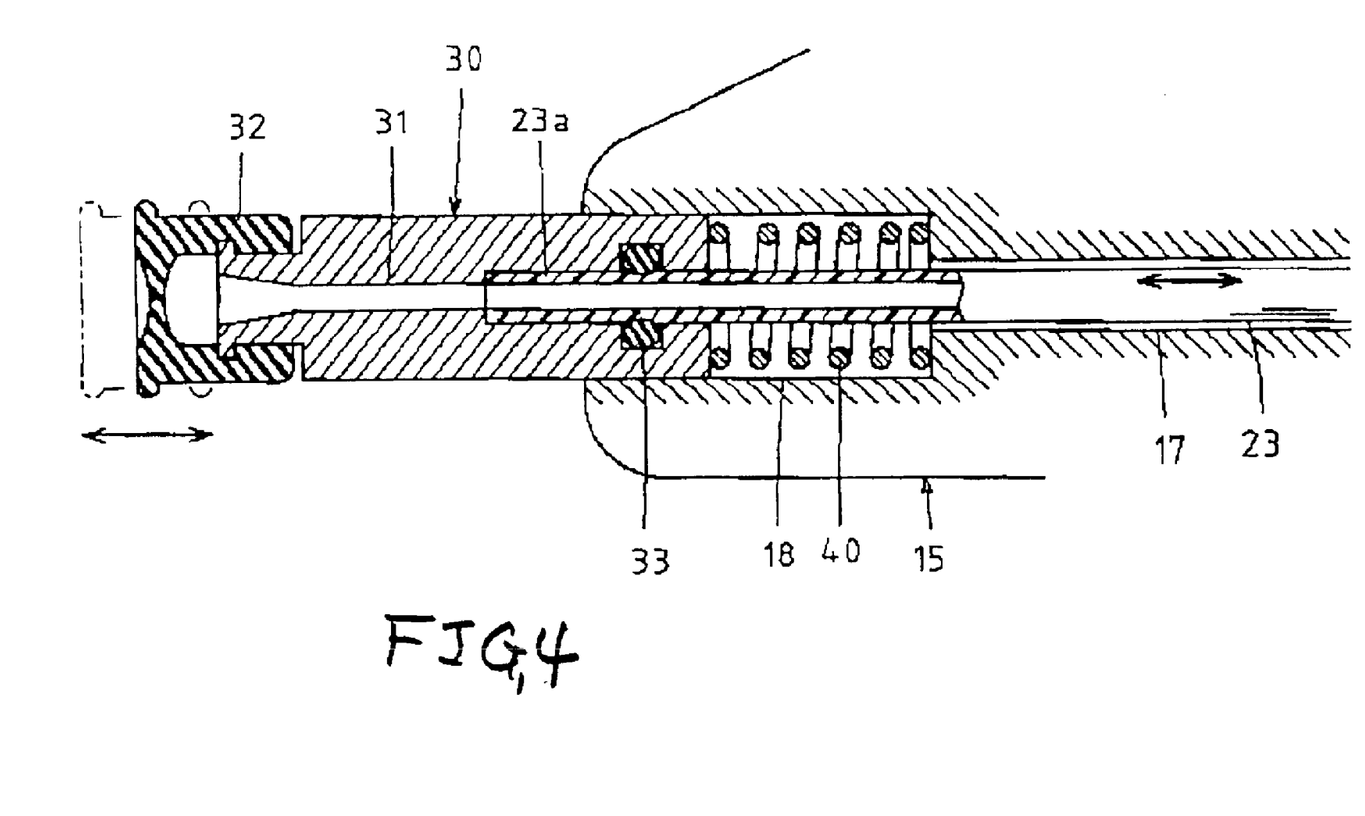
FIG. 4 is a partial section view of the vicinity of a basal end of a guide conduit in the used state of the outer sheathed endoscope of the first embodiment of the invention.

In the used state of the endoscope 10, at the same time when the outer sheath 20 covers the flexible insertion portions 11, 12, and 13, the flexible channel tube 23 is passed through the guide conduit 17. FIG. 4 shows the vicinity of the basal end of the guide conduit 17 in this sate.

A forward portion of the forceps port member 30 is fittingly inserted in an advanceable and retractable manner into a cylinder hole 18 which is formed as a deep countersunk hole in the basal end opening portion of the guide conduit 17. The basal end part 23a of the flexible channel tube 23 is fixed to the forceps port member 30 in an insertable and extractable manner. The reference numeral 31 denotes a forceps passage which is formed in the forceps port member 30.

An O-ring 33 for the purposes of sealing and click attachment is attached to the forceps port member 30 into which the basal end part 23a of the flexible channel tube 23 is inserted. The O-ring 33 is engaged with a circumferential groove which is formed in the outer peripheral face of the basal end part 23a of the flexible channel tube 23, thereby fixing the basal end part 23a of the flexible channel tube 23 to the forceps port member 30.

The flexible channel tube 23 is axially advanceable and retractable over the whole length of the guide conduit 17. The forceps port member 30 is always outwardly (leftward in FIG. 4) urged by a compression coil spring 40 placed in the cylinder hole 18. As a result, there arises a state where the flexible channel tube 23 is always pulled toward the forceps port member 30 by the urging force of the compression coil spring 40.

According to the configuration, when the bend portion 12 is bent by operating the bending operation knob 16 to exert an axial compression force on the flexible channel tube 23, the forceps port member 30 is moved along a direction in which the member outwardly protrudes from the cylinder hole 18 to absorb the compression force acting on the flexible channel tube 23.

By contrast, when an axial pulling force acts on the flexible channel tube 23, the forceps port member 30 is moved along a direction in which the member enters the cylinder hole 18 to absorb the pulling force acting on the flexible channel tube 23. As a result, an excessive force does not act on the flexible tube portion 11, the bend portion 12, etc.

Figure 5:
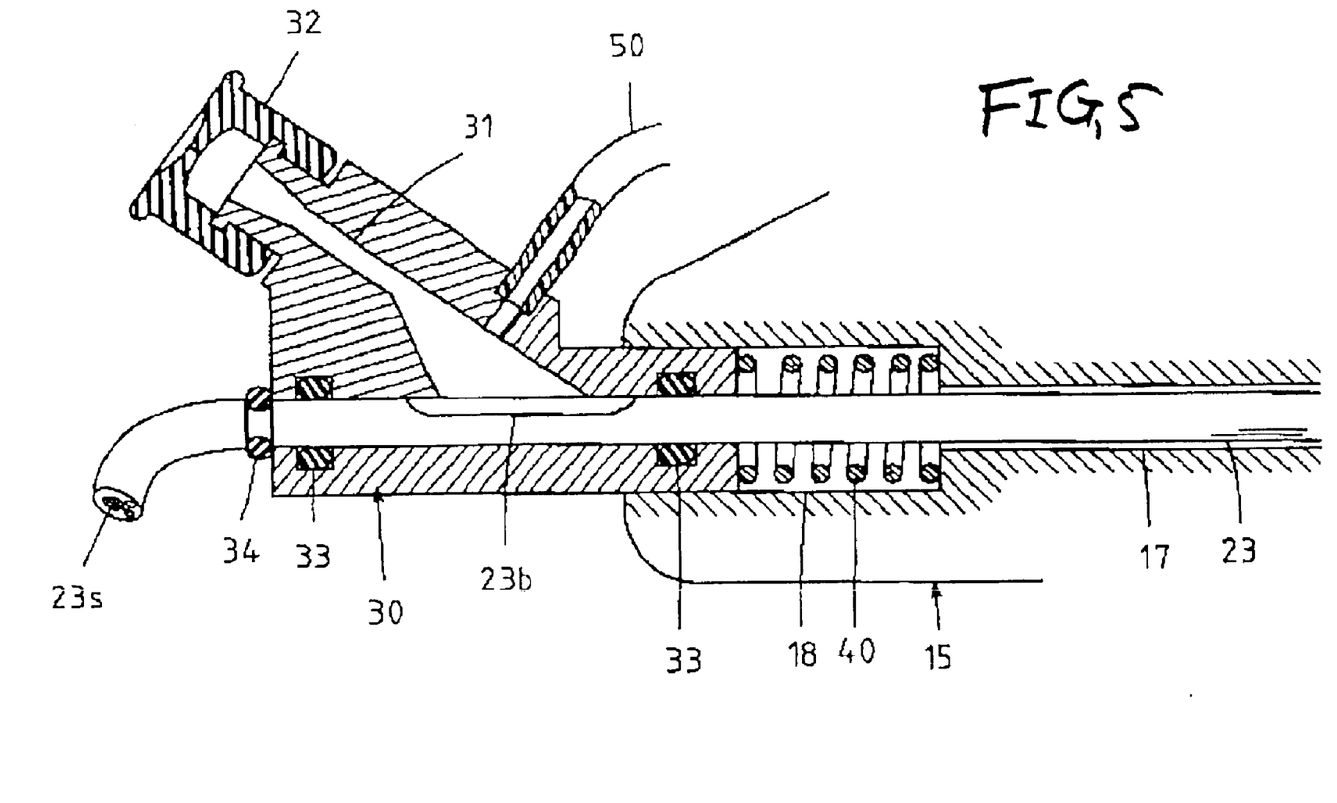
FIG. 5 is a partial section view of the vicinity of a basal end of a guide conduit in the used state of an outer sheathed endoscope of a second embodiment of the invention.

In the case where a so-called multi-lumen tube is used as the flexible channel tube 23, as shown in FIG. 5, the basal end part may be further elongated to the outside with being fixed to the forceps port member 30, and then connected to a gas and water feeding apparatus or the like which is not shown.

The reference numeral 34 denotes an engageable locking O-ring which restricts the guide conduit 17 from slipping off from the forceps port member 30, 23b denotes a side hole which is formed in the flexible channel tube 23 to communicate a forceps insertion hole (serving also as a suction port) of the flexible channel tube 23 with the forceps passage 31, 23s denotes a closing plug which closes an end of a lumen that is used for suction, and 50 denotes a suction tube.

According to the invention, a break prevention member which is formed by an elastic material is disposed to surround a basal end part of a flexible insertion portion, and an outer sheath is formed to cover continuously the flexible insertion portion and the break prevention member. In both a used state where the outer sheath is attached, and a stored state where the outer sheath is not attached, therefore, the flexible insertion portion does not easily buckle or break in the vicinity of a coupling portion with an operation portion, and excellent durability can be obtained.

Second Embodiment

FIGS. 6 to 9 show a second embodiment of the invention. The components identical with those of the first embodiment are denoted by the same reference numerals, and their description is omitted.

The second embodiment is different from the first embodiment in the configurations of the outer sheath and the break prevention member. Therefore, the second embodiment will be described with placing emphasis on the differences.

Figure 6:
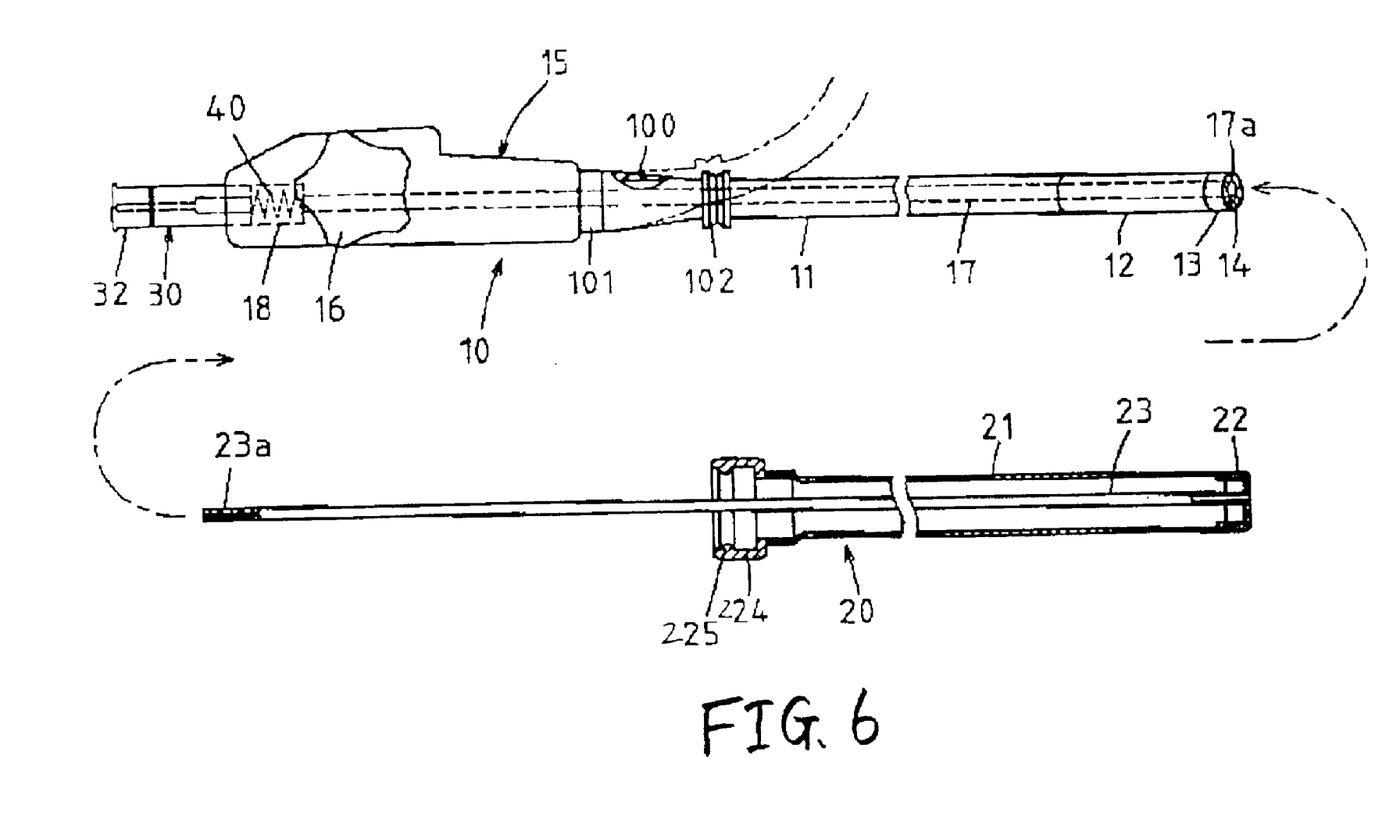
FIG. 6 is a side view partly in section showing the whole configuration of a stored state of an outer sheathed endoscope of a second embodiment of the invention.

A break prevention member attachment socket 101 made of a metal is disposed in a basal end part of the break prevention member 100. A sheath mounting seat 102 is molded integrally with a tip end part of the break prevention member 100.

A coupling ring 224 is fixed to the basal end of the cover tube 21. The coupling ring 224 is detachably engageable with the sheath mounting seat 102. An engagement protrusion 225 which protrudes from the inner face of the coupling ring 224 can be arbitrarily engaged and disengaged with the sheath mounting seat 102 having a circumferential groove-like shape.

Figure 7:
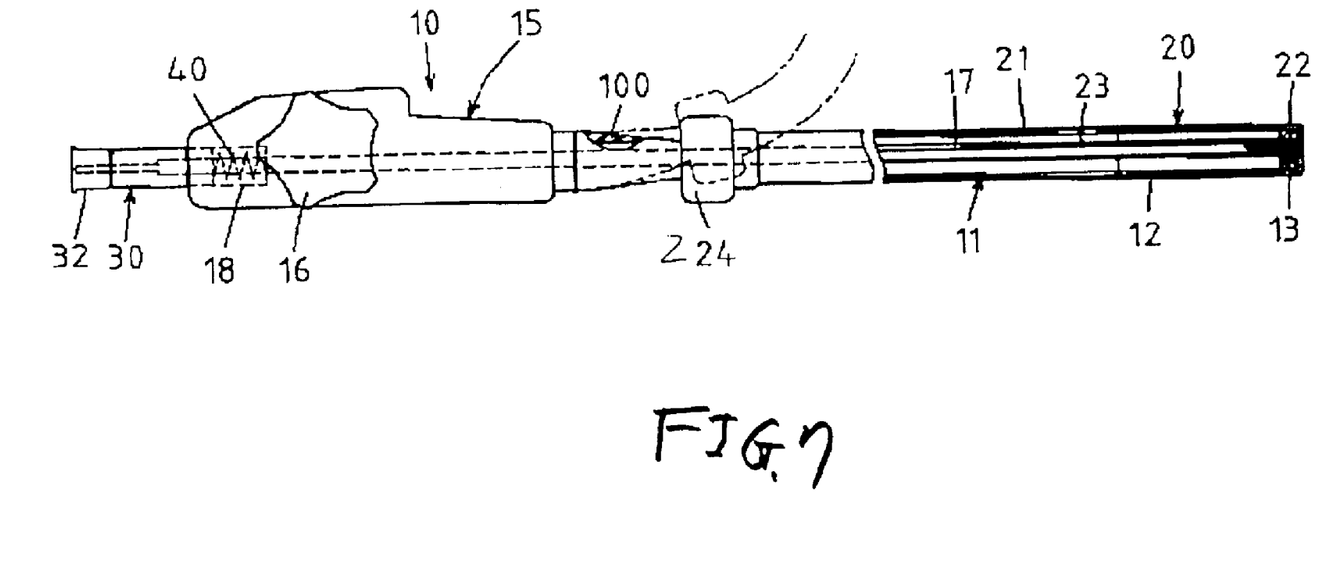
FIG. 7 is a side view partly in section showing the whole configuration of a used state of the outer sheathed endoscope of the second embodiment of the invention.

FIG. 7 shows the used state where the outer sheath 20 covers the flexible insertion portions 11, 12, and 13 of the endoscope 10 so that the end cap 22 abuts against the tip end face of the tip end body portion 13.

In this state, the coupling ring 224 disposed on the basal end of the outer sheath 20 is engaged with the sheath mounting seat 102 formed in the tip end part of the break prevention member 100 of the endoscope 10.

Figure 8:
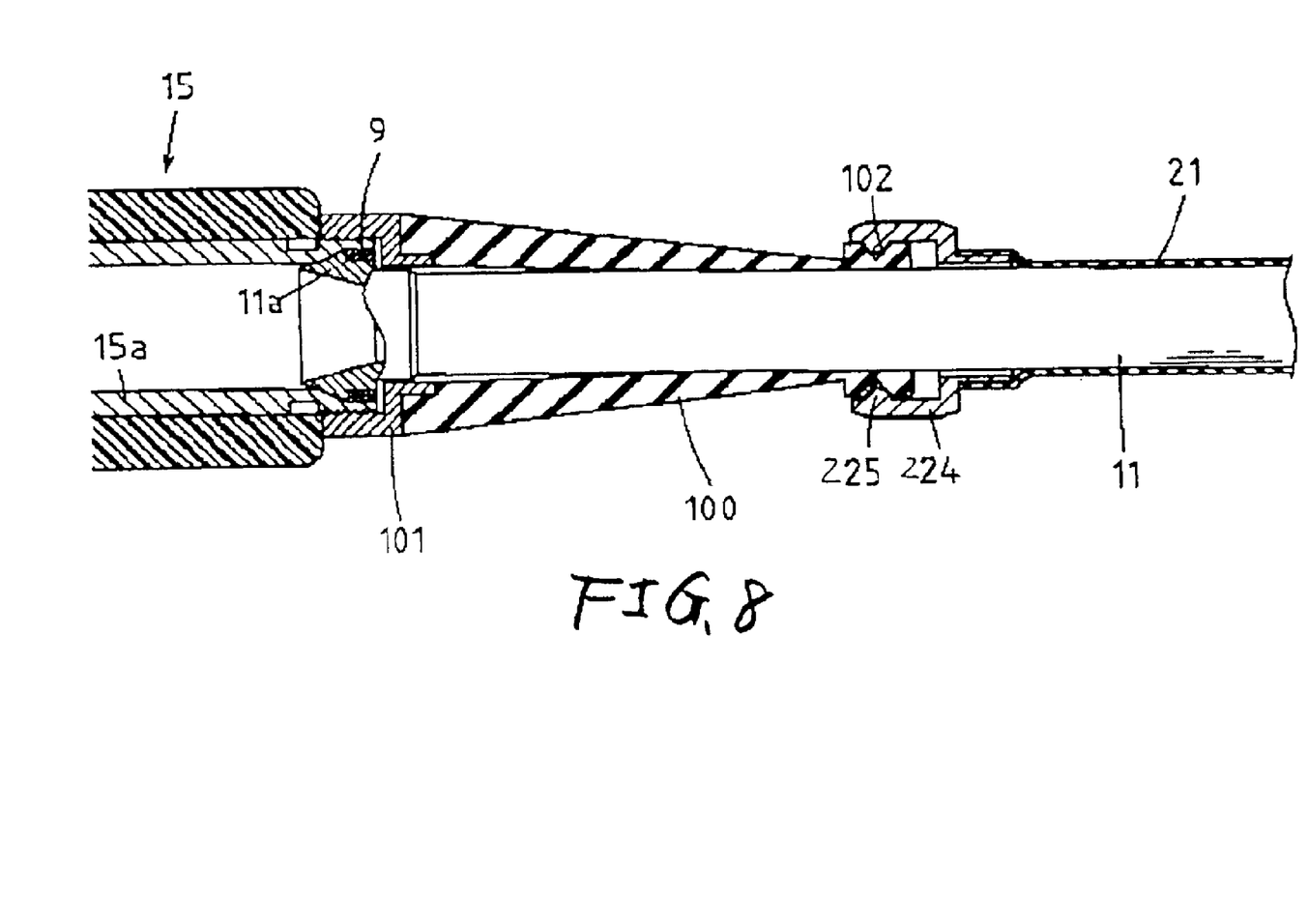
FIG. 8 is a side section view of the vicinity of a break prevention member in the used state of the outer sheathed endoscope of the second embodiment of the invention.

The break prevention member attachment socket 101 is integrated with the break prevention member 100, and screwed and fixed to the frame 15a of the operation portion 15. When the screw fixation is loosed, the break prevention member 100 can be detached.

In the embodiment, the sheath mounting seat 102 is the circumferential groove which has a V-like section shape, and which is formed in the outer peripheral face of the tip end part of the break prevention member 100, and the engagement protrusion 225 which is formed on the inner face of the coupling ring 224 is detachably engaged with the mounting seat. An operation of engaging or disengaging the engagement protrusion 225 with the sheath mounting seat 102 is performed by elastically deforming both or one of the coupling ring 224 and the sheath mounting seat 102.

In this way, the engagement protrusion 225 of the coupling ring 224 is engaged with the sheath mounting seat 102, whereby the flexible insertion portions 11, 12, and 13 of the endoscope 10 are fixed in the state where the portions are covered with the outer sheath 20, to be insulated from a contaminated area in a used state.

Figure 9:
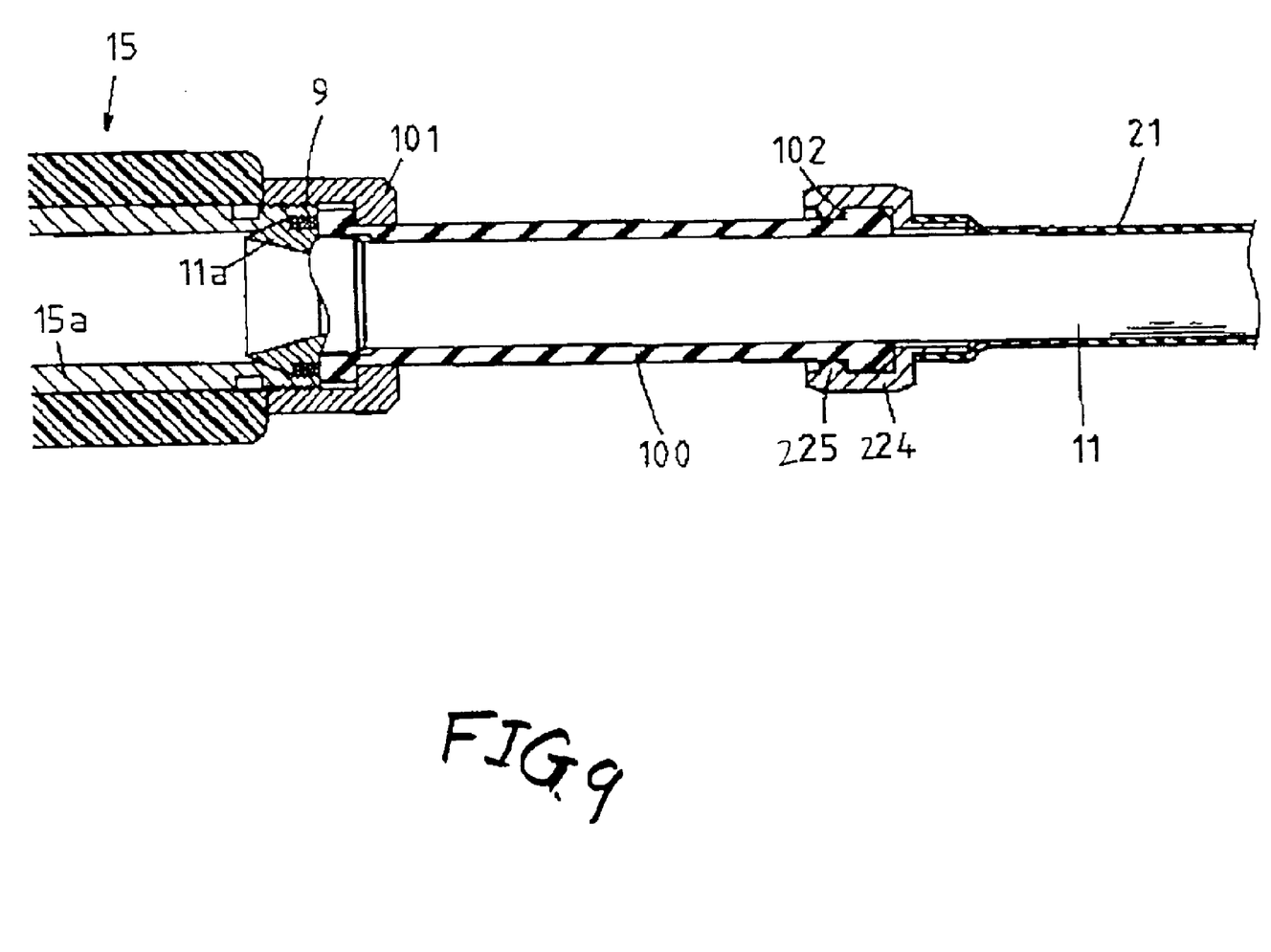
FIG. 9 is a side section view of the vicinity of a break prevention member in the used state of the outer sheathed endoscope of a modification of the second embodiment of the invention.

The invention is not restricted to the embodiments described above. For example, as shown in FIG. 9, the break prevention member 100 may have a cylindrical shape of a constant thickness, or another shape. The sheath mounting seat 102 may be a step or the like with which the engagement protrusion 225 formed on the coupling ring 224 can be detachably engaged. The break prevention member attachment socket 101 may be configured with being separated from the break prevention member 100.

According to the invention, a sheath mounting seat with which the basal end of an outer sheath is to be detachably engaged is formed on a tip end part of a break prevention member which is disposed to surround a basal end part of a flexible insertion portion. In both a used state where the outer sheath is attached, and a stored state where the outer sheath is not attached, the flexible insertion portion does not easily buckle or break in the vicinity of a coupling portion with an operation portion, and excellent durability can be obtained.

Third Embodiment

FIGS. 10 to 13 show a third embodiment of the invention. The components identical with those of the first embodiment are denoted by the same reference numerals, and their description is omitted.

The third embodiment is different from the first embodiment in the configurations of the outer sheath and the break prevention member. Therefore, the third embodiment will be described with placing emphasis on the differences.

Figure 10:
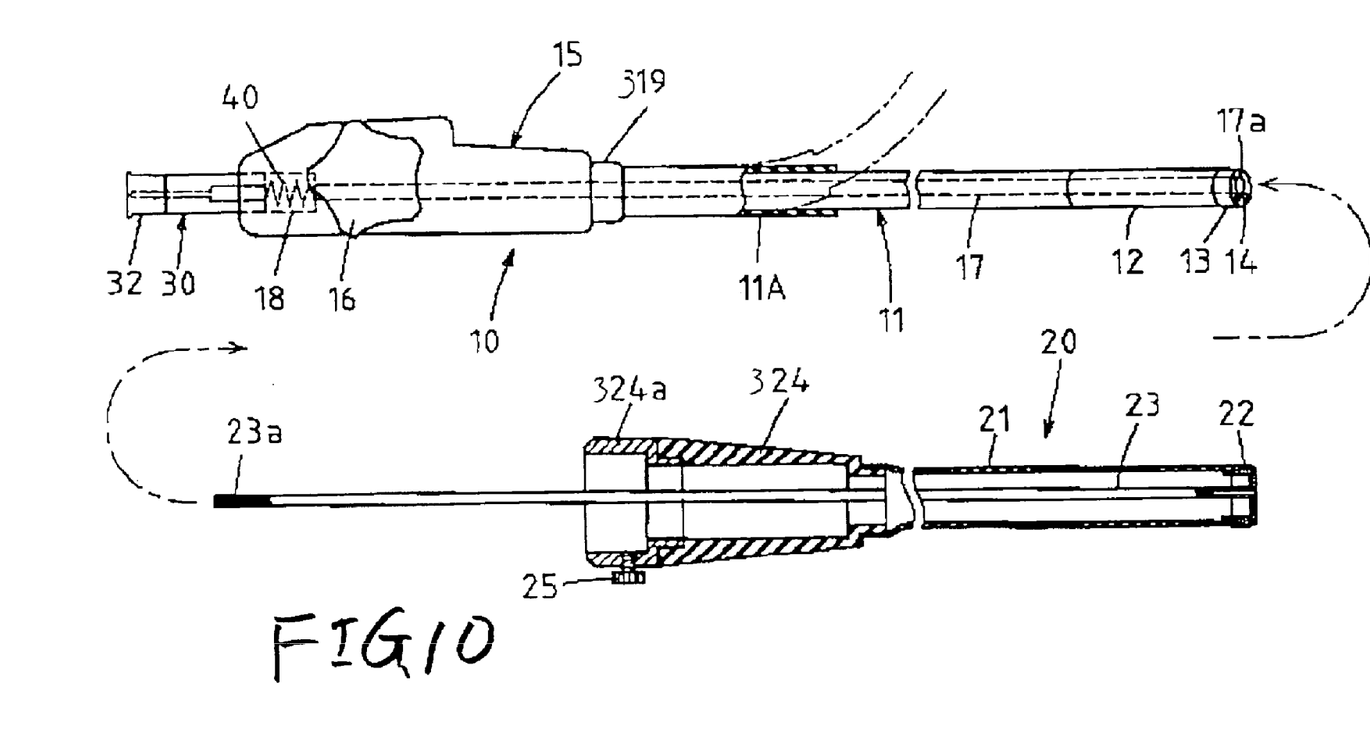
FIG. 10 is a side view partly in section showing the whole configuration of a stored state of an outer sheathed endoscope of a third embodiment of the invention.

A first break prevention member 11A which is made of an elastic material and has a cylindrical shape is attached to surround a basal end part of the flexible tube portion 11. The reference numeral 319 denotes a fixing ring which fixes the first break prevention member 11A to the operation portion 15.

As shown in detail in FIG. 12 which will be described later, the first break prevention member 11A is formed into a cylindrical shape in which the thickness is substantially constant as a whole. As indicated by the two-dot chain line in FIG. 10, even when the flexible tube portion 11 is bent in a stored state of the endoscope 10, because of the presence of the first break prevention member 11A, the first break prevention member 11A functions so as not to cause the coupling portion with the operation portion 15 to be sharply bent, thereby preventing the flexible tube portion 11 from buckling or breaking.

Figure 11:
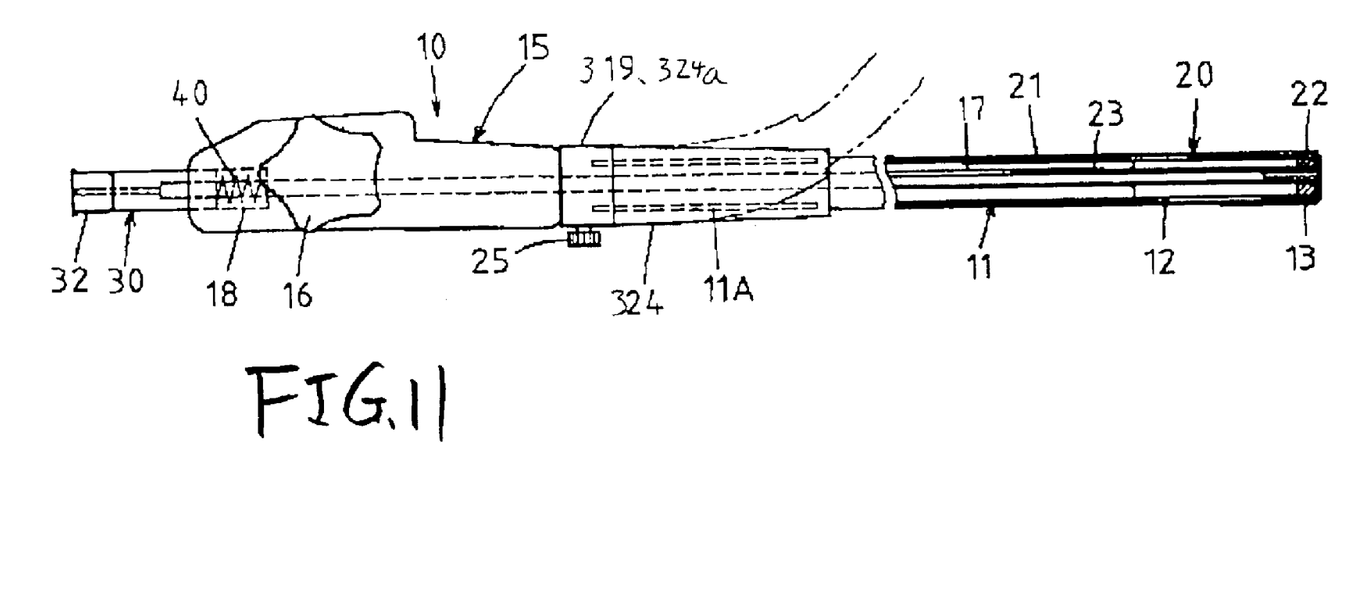
FIG. 11 is a side view partly in section showing the whole configuration of a used state of the outer sheathed endoscope of the third embodiment of the invention.

FIG. 11 shows the used state where the outer sheath 20 covers the flexible insertion portions 11, 12, and 13 of the endoscope 10 so that the end cap 22 abuts against the tip end face of the tip end body portion 13.

In this state, an attachment socket 324a of the outer sheath 20 is fixed to the fixing ring 319 of the endoscope 10, and a second break prevention member 324 of the cover tube 21 surrounds the first break prevention member 11A.

Figure 12:
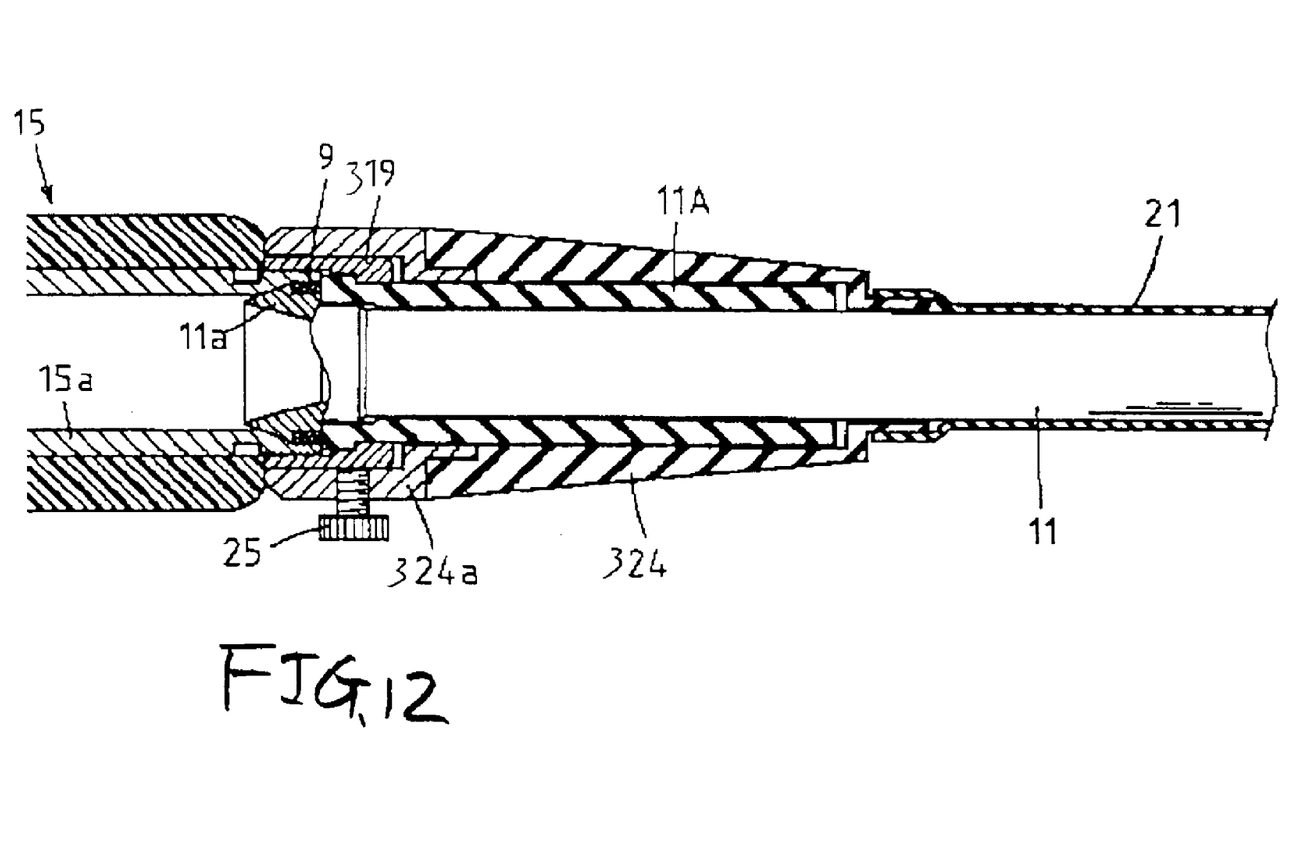
FIG. 12 is a side section view of the vicinity of a break prevention member in the used state of the outer sheathed endoscope of the third embodiment of the invention.

FIG. 12 shows in detail the vicinity of the first and second break prevention members 11A and 324 in this state. The incorporated articles such as the flexible channel tube 23 are not shown in the figure. In the flexible tube portion 11, the basal end socket 11a is fixed to the frame 15a of the operation portion 15 by the pressing ring 9 which is screwed to an end part of the frame 15a.

In the first break prevention member 11A, a collar portion which protrudes in a flange-like manner from the basal end is pressingly fixed to the frame 15a by the fixing ring 319 which is screwed with the frame 15a of the operation portion 15. The attachment socket 324a of the second break prevention member 324 is fixed to the fixing ring 319 by fastening a manual fixing screw 25 toward the outer peripheral face of the fixing ring 319. As a result, during a used state of the endoscope, not only the surface of the flexible tube portion 11 but also the first break prevention member 11A is insulated from a contaminated area.

In this state, the second break prevention member 324 is set to a position where it surrounds the first break prevention member 11A. As a result, as indicated by the two-dot chain line in FIG. 11, even when the flexible tube portion 11 of the endoscope 10 in a used state is bent, the first break prevention member 11A and the second break prevention member 324 function so as not to cause the coupling portion with the operation portion 15 to be sharply bent, thereby preventing the flexible tube portion 11 from buckling or breaking.

Since the first break prevention member 11A and the second break prevention member 324 are formed so as to radially overlap each other, the length can be shortened. Therefore, the root part of the operation portion 15 which is hardly bent is not much long, and hence excellent operability can be ensured.

Figure 13:
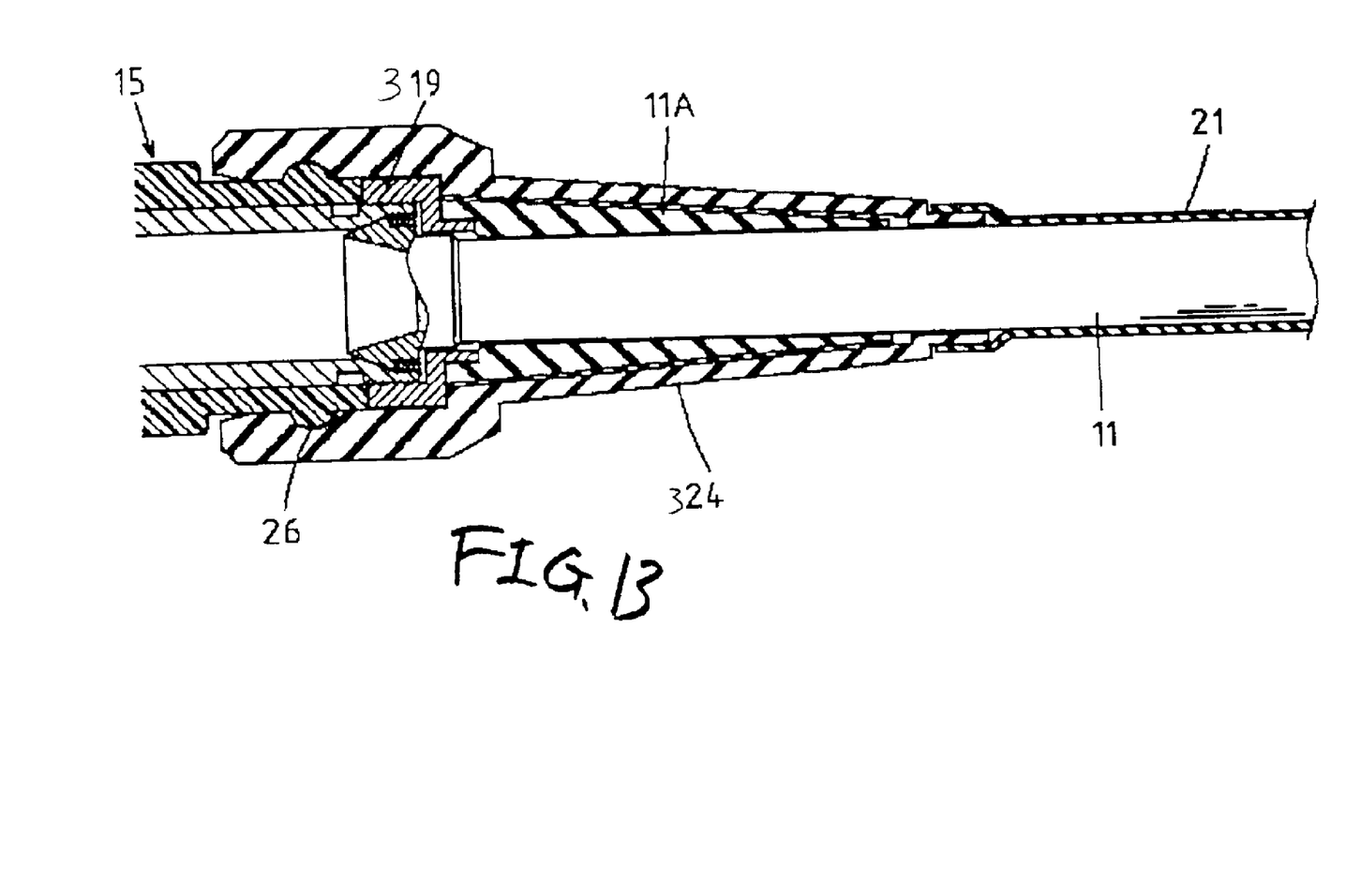
FIG. 13 is a side section view of the vicinity of a break prevention member in the used state of the outer sheathed endoscope of a modification of the third embodiment of the invention.

The invention is not restricted to the embodiments described above. For example, as shown in FIG. 13, the first break prevention member 11A may be formed into a tapered shape in which the thickness is gradually reduced as advancing toward the tip end, and the second break prevention member 324 may be formed so as to have a constant thickness. Alternatively, both the members may be formed into a shape in which the thickness is gradually reduced as advancing toward the tip end.

Alternatively, each of the first break prevention member 11A and the second break prevention member 324 may be formed so as to have a constant thickness while setting the material of a part on the side the tip end to be softer than that of a part on the side of the basal end.

According to the invention, a first break prevention member made of an elastic material is disposed to surround a basal end part of a flexible insertion portion, and a second break prevention member made of an elastic material is disposed in an outer sheath to surround the first break prevention member in a state where the outer sheath is attached to the flexible insertion portion. Therefore, a root part of an operation portion which is hardly bent is not required to be made very long, and, in both a used state where the outer sheath is attached, and a stored state where the outer sheath is not attached, the flexible insertion portion does not easily buckle or break in the vicinity of a coupling portion with an operation portion, and excellent durability and operability can be obtained.

What is claimed is:

1. An outer sheathed endoscope comprising:
   an operation portion;
   a flexible insertion portion, a basal end of which is connected to the operation portion;
   a first break prevention member comprising an elastic material, which is disposed to surround a basal end portion of the flexible insertion portion and is attached to the operation portion; and
   an outer sheath that shields the flexible insertion portion from an outside, said outer sheath detachably covering the flexible insertion portion and at least a part of the first break prevention member.

2. The outer sheathed endoscope according to claim 1, wherein the outer sheath continuously covers the flexible insertion portion and the first break prevention member.

3. The outer sheathed endoscope according to claim 1, wherein the first break prevention member is configured to have a tapered shape in which an outer diameter is gradually reduced, and the outer sheath is configured to have a shape in which the outer sheath in the vicinity of the basal end gradually spreads in as advancing toward an end part.

4. The outer sheathed endoscope according to claim 1, wherein the outer sheath covers the whole of the first break prevention member.

5. The outer sheathed endoscope according to claim 1, wherein the first break prevention member includes a sheath mounting seat which is detachably engaged with an end of the outer sheath.

6. The outer sheathed endoscope according to claim 5, wherein the sheath mounting seat is one of a groove and a step formed on an outer peripheral face of a tip end part of the first break prevention member.

7. The outer sheathed endoscope according to claim 5, wherein the sheath mounting seat and the first break prevention member are integral and are of a same material.

8. The outer sheathed endoscope according to claim 1, wherein the outer sheath includes a second break prevention member.

9. The outer sheathed endoscope according to claim 8, wherein the second break prevention member surrounds the first break prevention member when the outer sheath is attached to the flexible insertion portion.

10. The outer sheathed endoscope according to claim 8, wherein one of the first and second break prevention members has a constant thickness, and the other of the first and second break prevention members has a thickness which gradually decreases toward an end thereof.

11. The outer sheathed endoscope according to claim 1, wherein the outer sheath and the first break prevention member are of different materials.

* * * * *